United States Patent [19]

Filshie

[11] Patent Number: 5,318,548

[45] Date of Patent: Jun. 7, 1994

[54] MUCUS EXTRACTOR

[75] Inventor: Angus S. Filshie, Nottingham, England

[73] Assignee: Regent Limited, Nottingham, United Kingdom

[21] Appl. No.: 965,371

[22] PCT Filed: Jun. 26, 1991

[86] PCT No.: PCT/GB91/01032

§ 371 Date: Feb. 9, 1993

§ 102(e) Date: Feb. 9, 1993

[87] PCT Pub. No.: WO92/00111

PCT Pub. Date: Jan. 9, 1992

[30] Foreign Application Priority Data

Jun. 26, 1990 [GB] United Kingdom ............... 9014155

[51] Int. Cl.⁵ .................................................. A61M 1/00
[52] U.S. Cl. ............................................ 604/319; 604/35; 604/37

[58] Field of Search ................ 604/36, 37, 35, 319, 604/323, 73, 236, 216

[56] References Cited

U.S. PATENT DOCUMENTS

| 1,141,373 | 6/1915 | Behm | 604/315 |
| 1,925,230 | 9/1933 | Buckout | 604/37 |
| 3,892,226 | 7/1975 | Rosen | 604/37 |
| 5,024,653 | 6/1991 | Kohnke | 604/319 |
| 5,035,688 | 7/1991 | Inui | 604/319 |
| 5,062,835 | 11/1991 | Maitz et al. | 604/319 |
| 5,167,621 | 12/1992 | Band et al. | 604/319 |

Primary Examiner—Paul J. Hirsch
Attorney, Agent, or Firm—Finnegan, Henderson, Farabow, Garrett & Dunner

[57] ABSTRACT

The extractor (10) is particularly useful for extracting mucus from the nasal passages of new born babies and comprises a manually operable hand pump (18) with a separate compartment (12) for the mucus extracted.

6 Claims, 4 Drawing Sheets

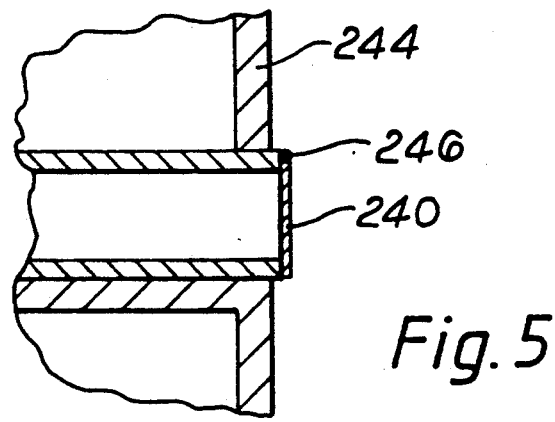
Fig. 3
Fig. 4
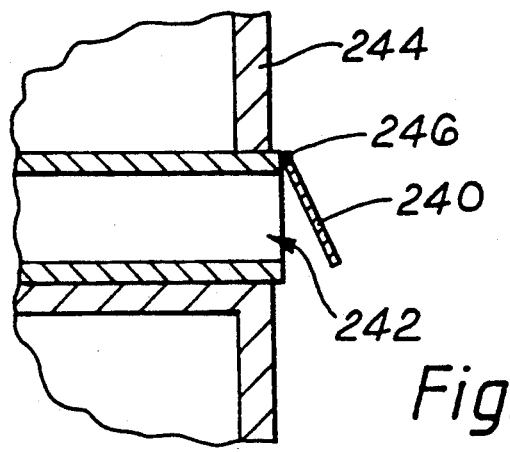
Fig. 5
Fig. 6

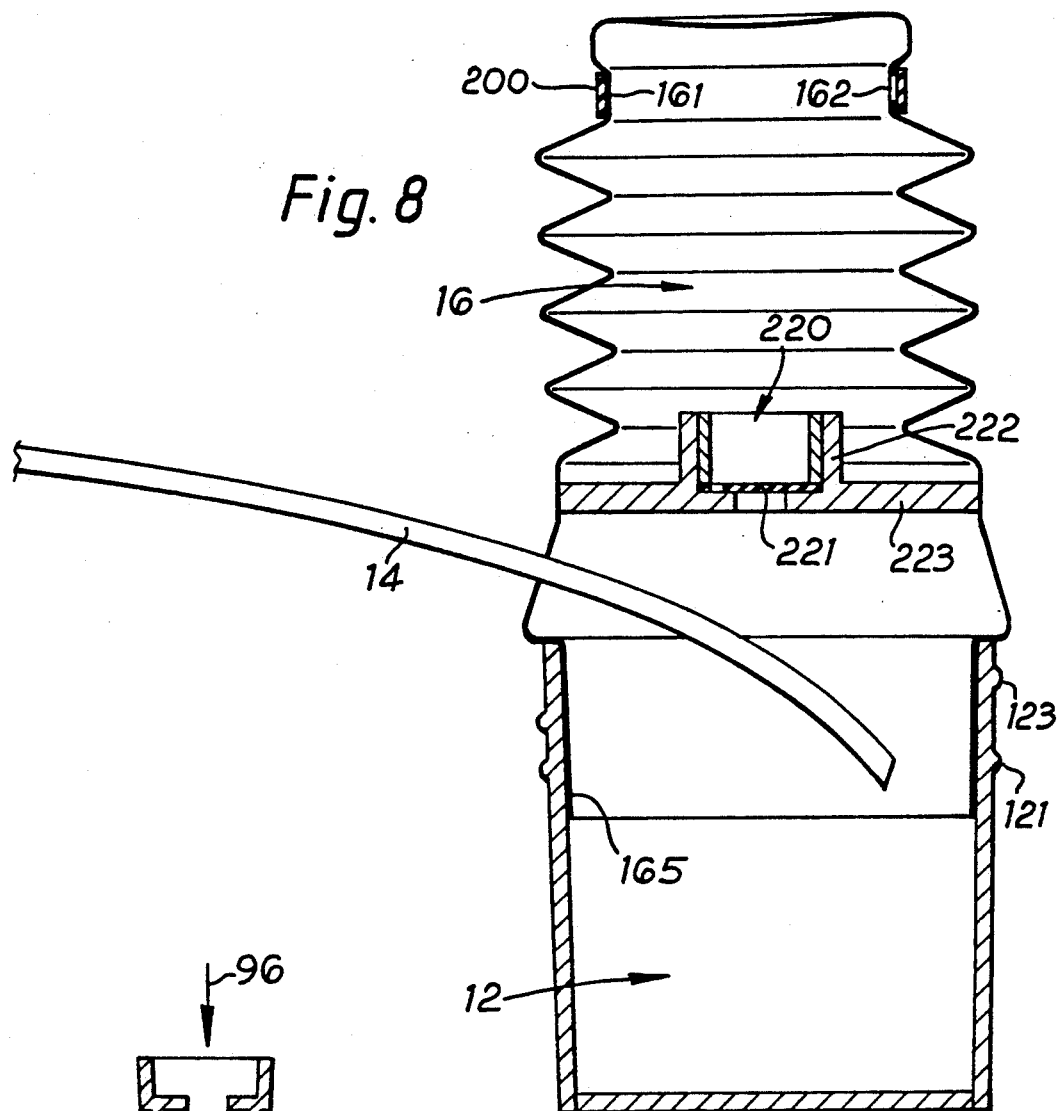
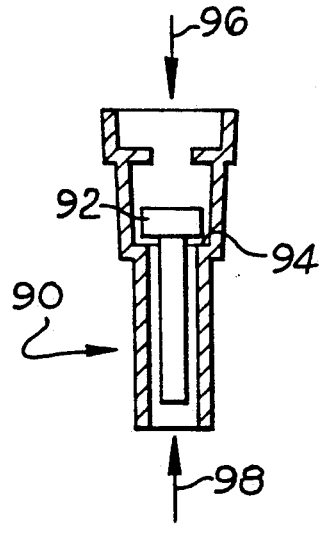
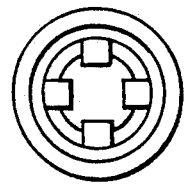
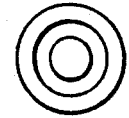
Fig. 8
Fig. 9
Fig. 10
Fig. 11

MUCUS EXTRACTOR

The present invention relates to mucus extractors and more particularly to a mucus extractor for newly born babies.

Babies when born often have their nasal passages blocked with mucus and it is necessary to clear these passages in such a manner that the baby will not be harmed. Known mucus extractors comprise a chamber with an inlet pipe and an outlet pipe. Suction provided by a Midwife is applied to the outlet pipe and the inlet pipe is inserted into the nasal passage. Though good control is achievable by a skilled Midwife the extractor is unsatisfactory because if too much suction is applied the Midwife can ingest some of the mucus. This can be dangerous if the baby is affected by one or more contagious diseases.

A further known extractor which avoids the above problem comprises a chamber with inlet tube and with an electrically driven suction pump, preferably battery powered. This though avoiding the above problem is expensive and often, when required in an emergency, the batteries are flat and fitting replacement batteries, even if available, is time-consuming.

It is an object of the present invention to provide a mucus extractor which avoids the above disadvantages, is relatively simple in construction and may be considered as a disposable item thereby avoiding any cross-contamination.

The present invention therefore provides an extractor for extracting mucus comprising a first chamber, inlet means for the chamber the inlet means being formed integrally with or being provided with a flexible pipe for insertion, in use, into the nasal passage of a baby, a second chamber the second chamber being flexible to enable the volume of air inside the chamber to be changed from a first to a second volume the second volume being smaller than the first volume, first one way valve means connecting the first and second chambers the first one way valve means allowing passage of air from the first chamber to the second chamber but not allowing passage of air from the second chamber to the first chamber, second one way valve means connecting the second chamber to the ambient air and being operative to allow passage of air from the second chamber to the ambient air but not allowing passage of air from the ambient air into the second chamber, characterised in that the first chamber is, in the normal upright operational position of the extractor, situated below the second chamber, in that the second chamber comprises a bellows like structure, in that the bellows like structure and the first container are formed to be in line with each other such that the extractor is able to be gripped by the digits of a single hand and in that the bellows are operable by a single digit of that hand and in that the inlet means is positioned below the first one way valve means to prevent contamination of the first valve means by the mucus and is positioned towards the top of the first chamber to enable, in the normal upright operation position of the extractor, the mucus to fall into the first chamber in a direction away from the first valve means and in that the second one way valve means is constructed within the bellows structure to be non blockable by the fingers of the hand when the device is operated.

In the present invention ambient air means the atmosphere surrounding the mucus extractor.

Preferably the extractor is made of plastics material.

In a preferred embodiment the first chamber may comprise two parts an upper and lower part, the lower part being removably attached to the upper part.

Embodiments of the present invention will now be described, by way of example with reference to the accompanying drawings, in which:

FIG. 3 shows a first one way valve for use in the embodiment of FIGS. 1 or 2 in a first closed position;

FIG. 4 shows the valve of FIG. 3 in a second open position;

FIG. 5 shows a second one way valve for use in the embodiment of FIG. 2 in a first closed position;

FIG. 6 shows the valve of FIG. 5 in a second open position;

FIG. 8 shows a further alternative embodiment of a mucus extractor according to the present invention; and FIGS. 9 to 11 show an alternative valve suitable for the present invention.

Figure 1:
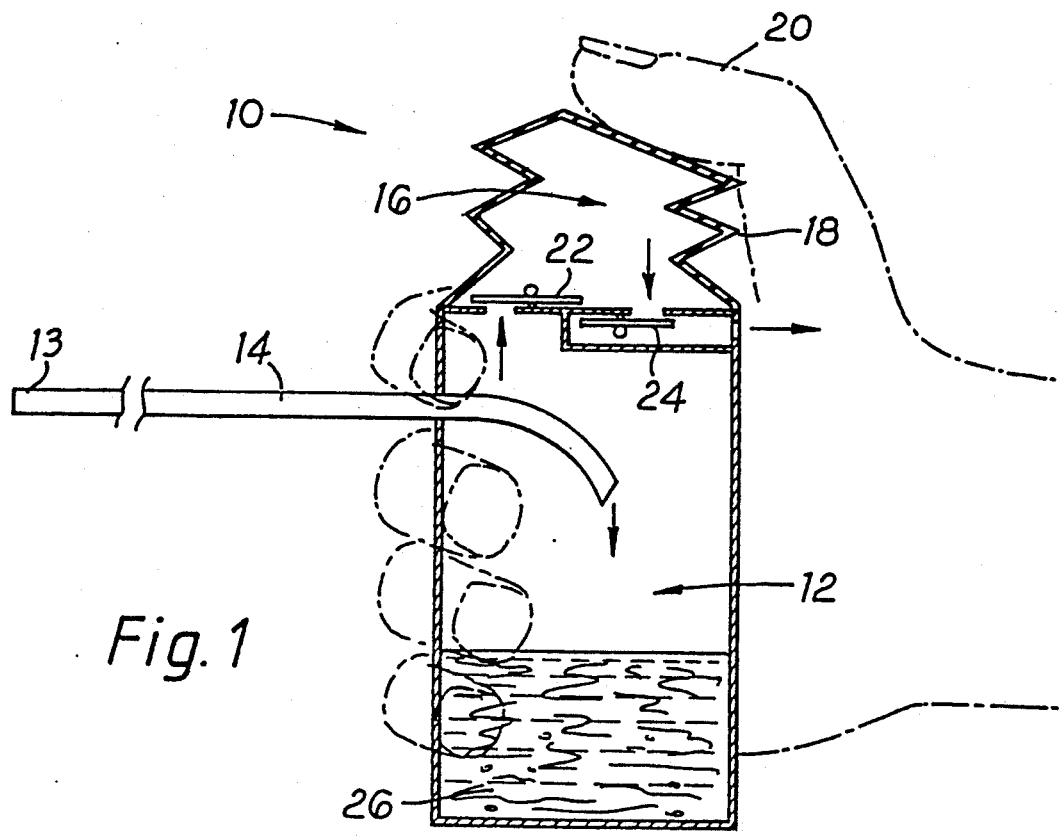
FIG. 1 shows a general schematic cross sectional side elevation view of a first mucus extractor according to the present invention illustrating the principle of operation.

With reference now to FIG. 1 the mucus extractor 10 comprises a first chamber 12, an inlet pipe 14 connected into the chamber 12 and being operative to have its far end 13 inserted into the nasal passage of a baby, in operation mucus being sucked along inlet pipe 14 into chamber 12.

Figure 2:
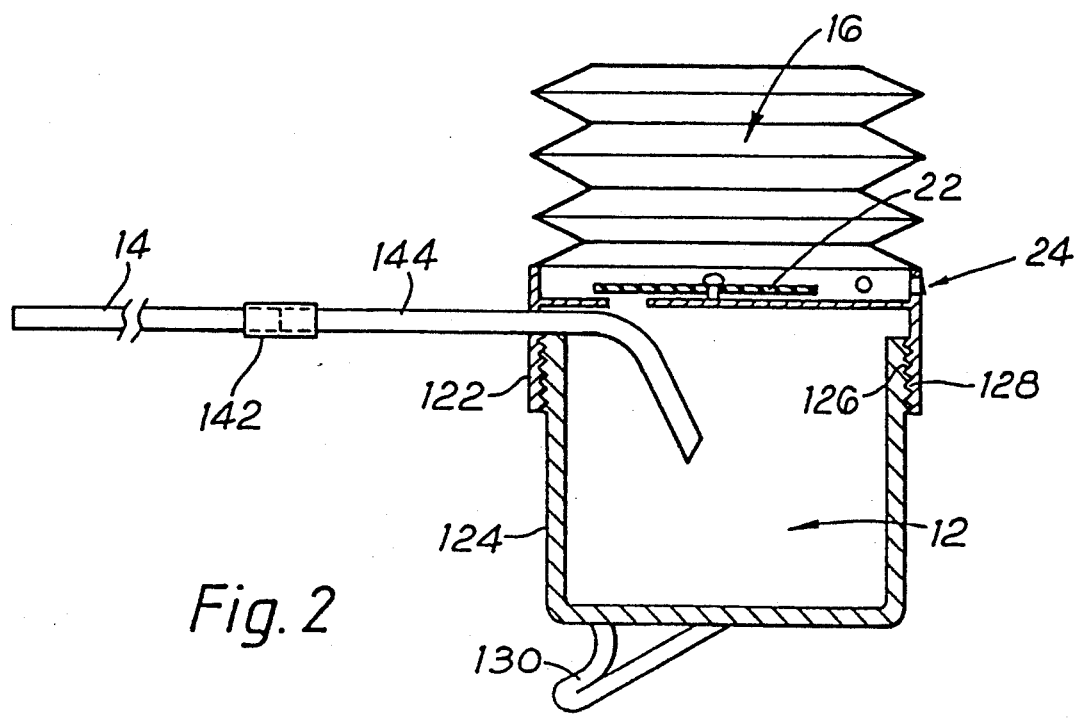
FIG. 2 shows a schematic side elevation view of a second mucus extractor according to the present invention.

A second chamber 16 is operatively connected to the first chamber and comprises a concertina bulb arrangement 18 which as shown may be compressed by a thumb 20 of an operator (not shown) and when released will return to its natural position (see FIG. 2).

A first one way valve 22 is positioned between chambers 12 and 16 and is operative to allow air to pass from the first chamber 12 to the second chamber 16 but not the opposite direction.

A second one way valve 24 is positioned between chamber 16 and the ambient air and is operative to allow air to be expelled from chamber 16 to the ambient air but not in the opposite direction.

The operation of the extractor is as follows. The end of the tube 14 is placed for example in the baby's nasal passage (not shown). Pressure is applied by thumb 20 to concertina bulb 18 to compress it. Air is expelled from chamber 16 to ambient air via valve 24. Pressure on thumb 20 is released and chamber 16 commences to expand back to its normal shape. Valve 24 closes and valve 22 opens thereby applying a negative pressure in chamber 12. This creates a partial vacuum along pipe 14 and mucus 26 is sucked along the tube and drawn into the lower part of chamber 12 as shown.

Concertina bulb 18 may in known manner be "pumped" to provided "prolonged" pressure along tube 14 in a series of pulses to unblock the nasal passage.

Advantages of the extractor according to the present invention are that because the negative air pressure is provided by the expansion of concertina bulb 18 this pressure is controlled. The mucus can only be discharged into chamber 12 and even if chamber 12 overflows it will only block valve 22. Thus there is no possibility of contamination and transfer of diseases to the Midwife or operator. The extractor is very simple to construct, it may be entirely made of plastics material and being relatively cheap to manufacture may be considered as a disposable unit.

Alternative by changing pipe means 14 to prevent cross-infection from a previous baby the extractor may be used again. In this respect the embodiment of FIG. 2 is advantageous with the lower chamber 12 being comprised of two parts 122, 124 which are in screw threaded engagement by co-operating male and female threads 126, 128. The pipe 14 may be joined as shown at joint 142 to a short pipe section 144 connected to the upper part 122 of chamber 12.

In the embodiment of FIG. 2 the lower part 124 of container 12 may, when filled, be removed by unscrewing and a separate screw top may then be provided to provide a sealed container which may be sent for analysis.

In the embodiment of FIG. 2 a finger grip 130 is provided enabling firmer gripping of the extractor. One way valves 22, 24 are modified and simplified as shown in FIGS. 3 to 6 as follows.

One way valve 22 shown in FIGS. 3 and 4 in a closed and open position comprises a flexible piece of material 220 provided with a hole 222 which enables it to be press filled over an upstanding knob 224, thus holding the material 220 in position adjacent to a valve port 226 in a wall 228 separating the upper and lower chambers 16 and 12.

When the bulb 18 is depressed the material 220 will be forced against valve port 226 and air will be expelled from chamber 16 via valve 24 (to be described hereafter). When bulb 18 is released air will be sucked from lower chamber 12 creating the required partial vacuum in this chamber for suction.

Valve 24 comprises a flap 240 hingedly mounted to cover a valve port 242 in the outer wall 244 of upper chamber 16. The hinge 246 may comprise a thinner section of the plastic from which flap 240 is preferably made.

In operation when bulb 18 is depressed valve flap 240 opens as shown in FIG. 6 to allow expulsion of air from chamber 16. When bulb 12 is released valve flap 240 closes against wall 244 to seal upper chamber 16 thus forcing open valve 22.

The valves 22, 23 are therefore readily made from plastics material, as is bulb 18 and lower chamber 12. Thus the extractors may be made relatively cheaply and therefore be a disposable item thereby removing any chance of contamination.

The extractor is, as illustrated, usable by one hand operation only leaving the operator's other hand for holding the baby and/or guiding the insertion of the tube 14. By suitable choice of plastics material for bulb 18 the suction pressure may be selected to be ideally suited for the required operation.

Figure 7:
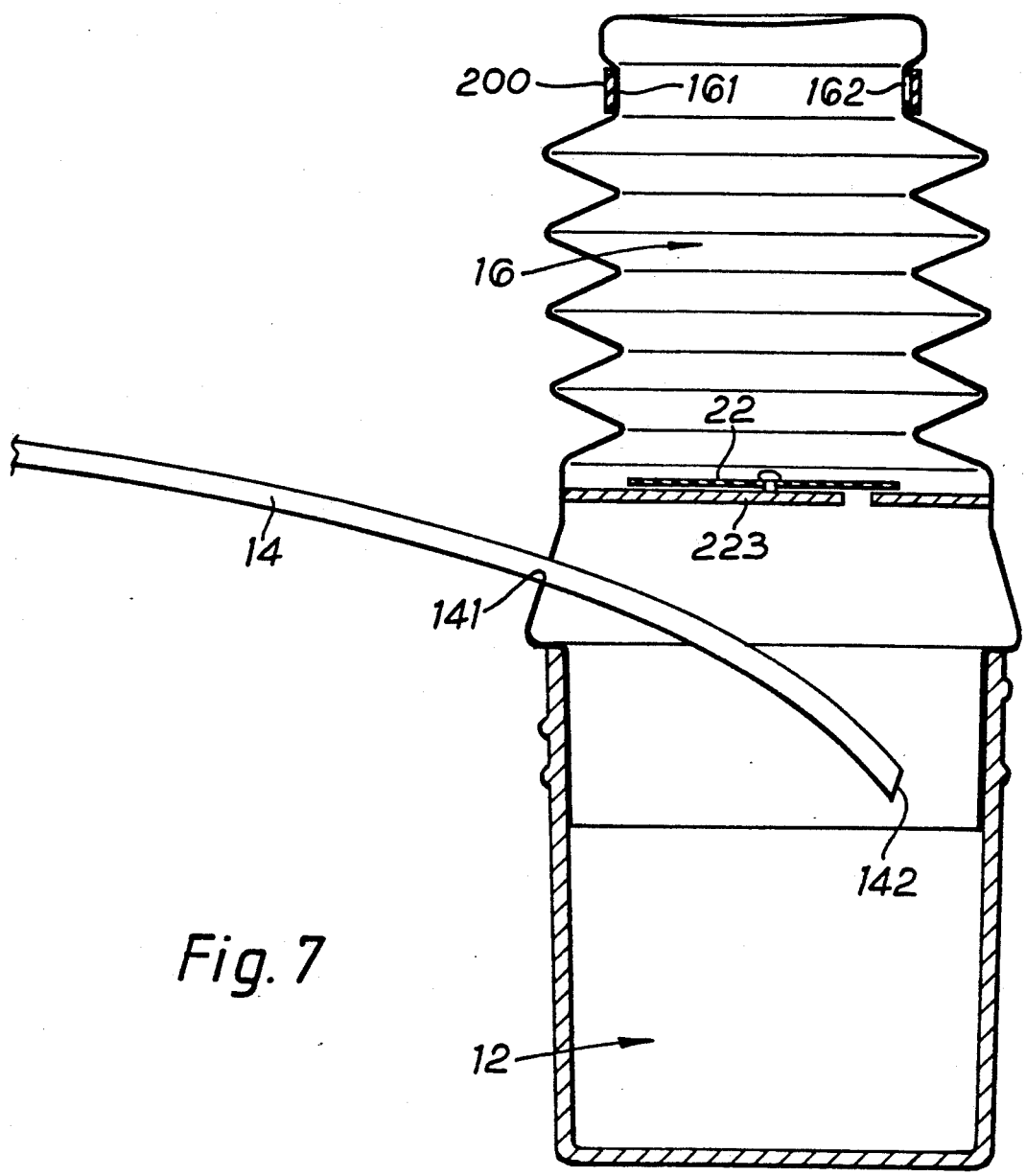
FIG. 7 shows an alternative embodiment of the mucus extractor according to the present invention.

With reference now to FIG. 7 an alternative embodiment is shown. Parts performing similar functions are given the same reference numerals as in FIG. 2. In this embodiment the outlet valve for the air from the bellow 16 is replaced by an arrangement comprising an elastic band 200 which is fitted at the top of the bellows 16 on a specifically designed flat wall portion 161. A hole (or holes) 162 is formed in the wall portion 161, this holding completely covered by elastic band 200. The elastic band is effective as a one way valve, denying entry of air into chamber 16 but allowing air to be expelled from chamber 16 into the atmosphere.

The tube 14 may be separate from the extractor and may be inserted into chamber 12 via a suitable hole 141 which may be of a slightly smaller diameter than tube 14. Alternatively tube 14 could be permanently attached by suitable means (eg by gluing, heat welding) and the length of the tube could be accommodated in the packaging by winding the tube around the extractor. The extractor and tube would be hermetically sealed in a readily openable "tear open" pack and the total package would be disposable.

The end 142 of tube 14 will be above the normal full level of the container 12 so that the mucus will not tend to block the end of tube 14. The container 12 will normally be made from clear plastics material to enable the operator to observe the level of the contents ensuring that the tube is not blocked. The valves 22 and 161, 162 are situated above the end 142 of tube 14 and thus there is little possibility of the valves becoming blocked. This is important since any reverse pressure along tube 14, which could be produced if valve 22 were "blocked" in an open position, could be extremely damaging.

With reference now to FIG. 8 an alternative embodiment to the extractor of FIG. 7 is shown. Parts performing similar functions are given the same reference numerals.

In this embodiment the inlet valve is replaced by a mylar valve arrangement 220 which comprises a flap 221 of mylar mounted in a valve socket arrangement 222 which is mounted on a partition wall 223. Partition wall 223 can therefore both in this embodiment and in the embodiment of FIG. 7 be a relatively simple structure and this renders possible the manufacture of the extractor by injection moulding and simple assembly technique.

The upper part may comprise (as in FIGS. 7 and 8) the bellows portion 16 and integrally formed therewith a skirt portion 165. The lower chamber 12 may comprise a suitable cylindrical receptacle provided with reinforcing bands 121, 123 and may be fitted to the skirt portion 165 as a push fitting thereby requiring no expensive assembly technique.

Lower chamber 12 may thus be detached from upper part 16 for example for analysis of the contents but will not be readily detachable during use.

With reference to FIGS. 9 to 11 an alternative simple one way valve means 90 to replace valve 220 is shown. This comprises a "floating" valve 92 which seals in one direction against a seating 94 when air pressure is applied in the direction of arrow 96 and releases to allow air to flow through when air pressure is applied in the direction of arrow 98.

The extractor is therefore extremely cheap to produce but because of the positioning of the outlet 141 of tube 14 below valve 22, 220 it is almost impossible for this valve to become contaminated. Preferably as shown tube end 141 is shaped to point away from valve 22, 220 so that contamination is further avoided.

I claim:

1. An extractor for extracting mucus comprising a substantially hollow cylindrical structure having a first chamber having a generally cylindrical outer wall and two opposed end walls in sealing attachment to said generally cylindrical outer wall, inlet means for the first chamber, the inlet means being formed integrally with or being provided with a flexible pipe for insertion, in use, into the nasal passage of a baby, a second chamber of flexible construction to enable the volume of air inside the second chamber to be changed from a first to a second volume with the second volume being smaller than the first volume, first one way valve means connecting the first and second chambers to allow passage of air from the first chamber to the second chamber but not allowing passage of air from the second chamber to the first chamber, second one way valve means connecting the second chamber to the ambient air and allowing passage of air from the second chamber to the ambient air but not allowing passage of air from the ambient air into the second chamber, wherein the first chamber is, in the normal upright operational position of the extractor, situated below the second chamber, the second chamber comprises a bellows structure, with the bellows structure and the first chamber formed to be in line with each other so that the extractor is able to be gripped by the digits of a single hand and the bellows are operable by a single digit of that hand and the inlet means is positioned below the first one way valve means to prevent contamination of the first valve means by extracted mucus and is positioned towards the top of the first chamber to enable, in the normal upright operation position of the extractor, the extracted mucus to fall into the first chamber in a direction away from the first valve means and the second one way valve means is constructed within the bellows structure to be nonlockable by the fingers of the hand when the device is operated.

2. An extractor for extracting mucus as claimed in claim 1, characterised in that the second one way valve means comprises a cylindrical wall portion of the bellows situated at an end of the bellows remote from the first chamber, in that the cylindrical wall portion is provided with at least one hole extending through the wall portion of the bellows and in that an elastic band is positioned external to the bellows to cover the at least one hole and to provide by virtue of the elasticity of the band said second one way valve means.

3. An extractor as claimed in claim 1 in which the extractor is made of plastics material.

4. An extractor as claimed in claim 1 in which the first chamber comprises two parts, an upper and lower part, the lower part being removably attached to the upper part.

5. An extractor as claimed in claim 1 in which both said first and second one way valve means comprise plastic flap means being operative to seal an opening against passage of air in one direction only.

6. An extractor as claimed in claim 5 in which the plastic flap comprising the first valve means comprises a flexible piece of plastics material provided with a hole therethrough, in which the second chamber includes a wall means separating the second chamber from the first chamber and in which the wall means includes an upstanding knob for co-operating with the hole through the flexible piece of plastics to retain the plastic flap in a desired position.

* * * * *

UNITED STATES PATENT AND TRADEMARK OFFICE
CERTIFICATE OF CORRECTION

PATENT NO. : 5,318,548
DATED : June 7, 1994
INVENTOR(S) : Angus S. Filshie

It is certified that error appears in the above-indentified patent and that said Letters Patent is hereby corrected as shown below:

Claim 1, column 5, lines 25-26, "nonlockable" should read --nonblockable--.

Signed and Sealed this

Eighth Day of November, 1994

Attest:

BRUCE LEHMAN

Attesting Officer     Commissioner of Patents and Trademarks